United States Patent [19]

Spatz

[11] Patent Number: 4,596,813

[45] Date of Patent: Jun. 24, 1986

[54] PYRIDYLCARBONYL AND THIOCARBONYL DERIVATIVES USEFUL AS FUNGICIDES

[75] Inventor: David M. Spatz, Fairfax, Calif.

[73] Assignee: Chevron Research Company, San Francisco, Calif.

[21] Appl. No.: 439,242

[22] Filed: Nov. 4, 1982

[51] Int. Cl.$^4$ .................... A01N 43/40; C07D 213/40
[52] U.S. Cl. .................................. 514/355; 514/354; 546/313; 546/316; 546/323; 544/335; 544/406; 548/343
[58] Field of Search ...................... 546/313, 316, 323; 540/225; 514/354–355

[56] References Cited

U.S. PATENT DOCUMENTS 4,191,770  3/1980  Liepmann et al. .............. 546/323 X
4,267,335  5/1981  McGill .............................. 546/257

OTHER PUBLICATIONS

Nonoyama et al., *Chem. Abstracts*, vol. 76: 9969z, (1972).
Singh et al., *Indian J. Pharm.*, 30(10), pp. 231-233.
*The Merck Index*, 9th ed., Merck and Co., Inc., Rahway, N.J., (1976), p. 644, abstract 4761.

*Primary Examiner*—Donald G. Daus
*Assistant Examiner*—William A. Teoli, Jr.
*Attorney, Agent, or Firm*—D. A. Newell; T. G. DeJonghe; S. L. Biggs

[57] ABSTRACT

The substituted heteroaryl compounds of this invention are good fungicides. In particular, they possess especially good activity against Bean Powdery Mildew, and other plant fungal diseases.

16 Claims, No Drawings

PYRIDYLCARBONYL AND THIOCARBONYL DERIVATIVES USEFUL AS FUNGICIDES

BACKGROUND OF THE INVENTION

This invention is drawn to novel fungicides.

With the world more dependent for food on an ever decreasing amount of cultivated farmland, it is increasingly important to develop effective fungicides which protect crops from fungicidal destruction.

Kozlik et al, in CA 79:53324Z, disclosed 1-carbamolyimidazoles as insecticidal.

Brookes et al, in U.S. Pat. Nos. 4,080,462 and 3,991,071, disclosed 1-(N,N-disubstituted carbamoyl and thiocarbamoyl)-imidazoles as fungicidal.

SUMMARY OF THE INVENTION

The compounds of the present invention are represented by the formula:

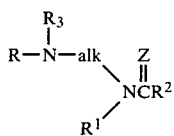

wherein R is phenyl, or phenyl substituted with 1 to 3 substituents independently selected from fluoro, chloro, bromo, iodo, nitro, lower alkyl, lower alkoxy, lower alkyl or lower alkoxy substituted with 1 to 3 of the same or different halogens; $R^1$ is lower alkyl, or —$CH_2Y$ wherein Y is lower alkenyl, lower alkenyl substituted with 1 to 3 of the same or different halogens, lower alkynyl, lower alkynyl substituted with 1 to 3 of the same or different halogens, lower alkoxyalkyl, lower alkoxy, lower alkyl-thioalkyl, lower thioalkyl, lower hydroxyalkyl, lower haloalkyl, or halogen; $R^2$ is a 6-member heterocyclic ring containing 1 to 2 nitrogen atoms and the remainder carbon atoms, a 6-member heterocyclic ring containing 1 to 2 nitrogen atoms and the remainder carbon atoms with the ring substituted with 1 to 2 independent lower alkyl groups, a 5-member heterocyclic ring containing 1 to 2 nitrogen atoms and the remainder carbon atoms, or a 5-member heterocyclic ring containing 1 to 2 nitrogen atoms and the remainder carbon atoms with the ring substituted with 1 to 2 independent lower alkyl groups, with the proviso that a nitrogen of the 5- or 6-member heterocyclic ring is not bonded to the

group; $R^3$ is hydrogen or lower alkyl; Z is sulfur, or oxygen; and alk is a branched- or straight-chain alkylene group of 1 to 10 carbons with the proviso that the chain length is no longer than 5 carbons.

Among other factors, the present invention is based on my finding that the compounds of this invention are effective fungicides. In particular, some of the compounds of this invention possess good activity against Bean Powdery Mildew.

In part due to their superior fungicidal activity, preferred R groups include the trihalophenyl and dihalophenyl groups. Particularly preferred R groups are 2,4,6-trihalophenyl and 2,6-dihalophenyl.

Preferred halogens include bromo and chloro.

Preferred $R^1$ groups include, for instance, lower hydroxyalkyl, lower alkyl and lower alkenyl groups. A particularly preferred $R^1$ group is lower alkyl. Most preferably $R^1$ is ethyl or n-propyl.

Preferred $R^2$ groups include, for instance, 3-pyridyl, 5-pyrimidyl, 2-pyrazyl and 5-(1-methylimidazolyl).

Preferred alk groups include, for instance, methylene, ethylene, propylene, 1-methylethylene, and the like. Most preferably, alk is ethylene.

DEFINITIONS

As used herein, the following terms have the following meanings, unless expressly stated to the contrary.

The term "alkenyl" refers to unsaturated alkyl groups having a double bond [e.g., $CH_3CH=CH(CH_2)_2$—,] and includes both straight- and branched-chain alkenyl groups.

"Lower alkenyl" groups refer to alkenyl groups having from 2 through 6 carbon atoms. Typical lower alkenyl groups include, for example, ethylene, but-3-enyl, hex-4-enyl, 2-methylpent-4-enyl, and the like.

The term "alkynyl" refers to unsaturated alkyl groups having a triple bond [e.g., $CH_3\equiv C(CH_2)_2$—] and includes both straight- and branched-chain alkynyl groups.

The term "lower alkynyl" refers to alkynyl groups having from 2 through 6 carbon atoms and includes, for example, but-3-ynyl, hex-4-ynyl, 3-methylpent-4-ynyl, and the like.

The term "alkyl" refers to both straight- and branched-chain alkyl groups. Generally, such alkyl groups contain from 1 through 12 carbon atoms.

The term "lower alkyl" refers to both straight- and branched-chain alkyl groups having a total from 1 through 6 carbon atoms and includes primary, secondary and tertiary alkyl groups. Typical lower alkyls include, for example, methyl, ethyl, n-propyl, isopropyl, n-butyl, t-butyl, n-hexyl, and the like.

The term "halo" or "halogen atom" refers to the groups fluoro, chloro, bromo and iodo.

The term "alkoxy" refers to the group R'O— wherein R' is alkyl.

The term "lower alkoxy" refers to the alkoxy groups having from 1 through 6 carbon atoms and includes, for example, methoxy, ethoxy, t-butoxy, hexoxy, and the like.

The term "lower alkoxyalkyl" refers to groups having the formula R"OR'''— wherein R" and R''' are independently lower alkyl. Typical lower alkoxyalkyl groups include, for instance, methoxymethyl, methoxypropyl, isopropoxybutyl, hexoxyhexyl, and the like.

The term "lower hydroxyalkyl" refers to the group HOR"— wherein R" is lower alkyl. Such groups include, for example, hydroxymethyl, hydroxyethyl, hydroxyhexyl, and the like.

The term "thioalkyl" refers to the group having the formula R'S— wherein R' is alkyl.

The term "lower thioalkyl" refers to such alkylthio groups wherein the alkyl groups is a lower alkyl. Typical lower alkyl groups include, for example, methylthio, ethylthio, t-butylthio, and the like.

The term "lower alkylthioalkyl" refers to the group R"SR'''— wherein R" and R''' are independently lower alkyl. Typical lower alkylthioalkyl groups include, for instance, methylthiomethyl (e.g., $CH_3SCH_2$—), ethylthiomethyl (e.g., $CH_3CH_2SCH_2$—), and the like.

The term "haloalkyl" refers to alkyl groups having one or more halo substituents. Typical haloalkyl groups include, for example, trifluoromethyl, dichloromethyl, bromochloromethyl, 1,2-dibromoethyl, 3-iodopropyl, chloromethyl, and the like.

The term "a 6-member heterocyclic ring containing 1 to 2 nitrogens" refers to the groups pyridyl, pyridazinyl, pyrimidyl, pyrazinyl, and the like.

The term "a 5-member heterocyclic ring containing 1 to 2 nitrogens" refers to the groups imidazolyl, pyrrolyl, pyrazolyl and the like.

The term "alk" refers to straight- and branched-chain alkylene groups of 1 to 10 carbons and includes, for instance, ethylene, propylene, 2-methylpropylene

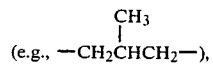

3-methylpentylene

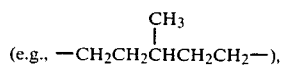

and the like.

The term "ethylenediamine" refers to the group $H_2NCH_2CH_2NH_2$.

The term "N'-(n-propyl), N'-(3-pyridylcarbonyl) ethylenediamine" refers to the group:

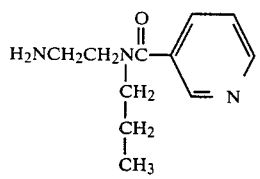

The term "N-(2,4,6-trichlorophenyl)-N'-(n-propyl), N'-(3-pyridylcarbonyl) ethylenediamine refers to the group:

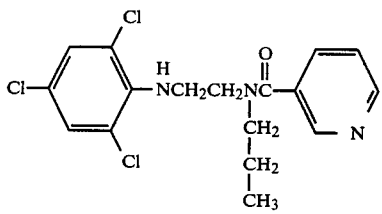

The term "nicotine amide" refers to the group:

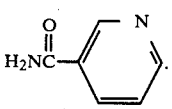

The term "pyrazinamide" refers to the group:

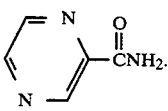

DETAILED DESCRIPTION OF THE INVENTION

The compounds of this invention are prepared according to the following synthetic scheme:

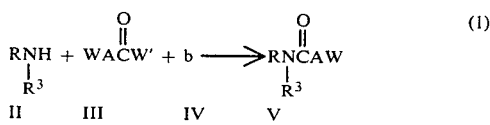

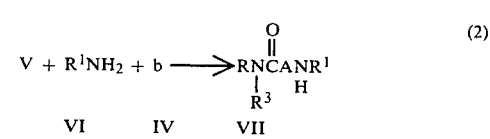

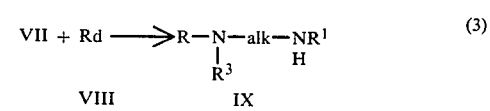

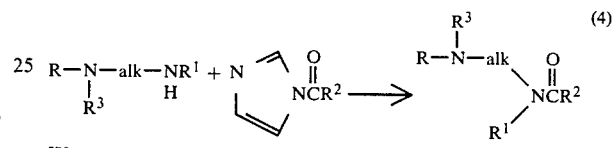

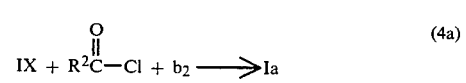

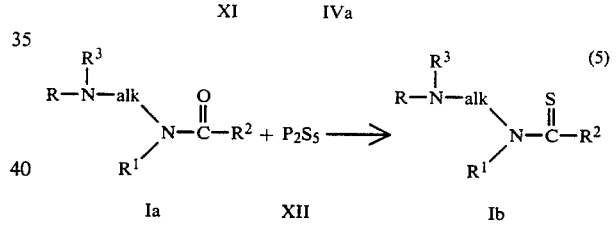

wherein R, $R^1$, $R^2$, $R^3$, and alk are as defined above; W and W' are independently halogen, b is a base, $b_2$ is an acid scavenger (base), and A is a straight- or branched-chain alkylene group 1 carbon shorter in length than the resulting alk group.

Reaction (1) is conducted by adding an essentially equimolar amount of a haloalkyl acid halide, III, to II. The reaction is conducted in the liquid phase employing an aprotic anhydrous organic solvent such as chloroform, methylene chloride, toluene, and the like. An essentially equimolar amount of a base, IV, is added to the system to scavenge the acid generated during the reaction. Preferably, an organic base such as a trialkylamine (e.g., triethylamine), pyridine, and the like is employed. Reaction pressure is not critical and for convenience, the reaction is conducted at atmospheric pressure. The reaction is generally conducted at from −20° C. to 80° C., although preferably at from 0° C. to 25° C., and is generally complete from within 1 to 24 hours. The resulting amide, V, is then isolated by conventional procedures such as extraction, filtration, chromatography, distillation, or alternatively, is used in Reaction (2) without purification and/or isolation.

Reaction (2) is conducted by adding an essentially equimolar amount of the appropriate primary amine, VI, to V. An essentially equimolar amount of a base, IV, is added to the system in order to scavenge the acid generated during the reaction. Preferably, an organic base such as a trialkylamine (e.g., triethylamine), pyridine, and the like is employed. The reaction is done in the liquid phase using an inert anhydrous organic solvent such as chloroform, methylene chloride, dimethoxyethane, and the like. Alternatively, in lieu of adding solvent and base, the reaction may be accomplished by using an excess of primary amine. Reaction pressure is not critical and for convenience, the reaction is generally conducted at atmospheric pressure. The reaction is generally conducted at from 0° C. to 100° C., although preferably at from 20° C. to 50° C., and is generally complete from within 1 to 24 hours. The product, VII, is isolated by conventional procedures such as extraction, filtration, chromatography, distillation, or alternatively, used in Reaction (3) without isolation and/or purification.

Reaction (3) is a conventional reduction of the amide to the amine.

In preparing compounds of this invention wherein the carbonyl of the amide is reduced to the methylene group, the reaction is conveniently conducted by adding an essentially equimolar amount of a reducing agent, $R_d$, to VIII. The reaction is conducted in the liquid phase employing an inert anhydrous organic solvent such as toluene, benzene, and the like. Suitable reducing agents include, for instance, lithium aluminum hydride, borane, borane methyl sulfide, and the like. Preferably, due to the ease in handling the reagent, borane methyl sulfide is employed as the reducing agent. However, when $R^1$ is a group susceptible to an undesired reaction with borane or borane methyl sulfide (such as allyl, propargyl, and the like), the preferred reducing agent is lithium aluminum hydride. Reaction pressure is not critical and for convenience, the reaction is conducted at atmospheric pressure. The reaction is generally conducted at from 0° C. to 110° C., although preferably at from 30° C. to 70° C., and is generally complete from within 1 to 24 hours. The resulting amine, IX, is isolated by conventional procedures such as extraction, filtration, chromatography, distillation, or alternatively, used in Reaction (4) without purification and/or isolation.

Reaction (4) is conducted by first preparing reagent X. X is prepared by adding an essentially equimolar amount of carbonyldiimidazole to the appropriate acid, $R^2CO_2H$ wherein $R^2$ is as defined above. The reaction is conducted in the liquid phase using an inert anhydrous organic solvent such as chloroform, methylene chloride, dimethoxyethane, toluene, and the like. Reaction pressure is not critical and for convenience, the reaction is generally conducted at atmospheric pressure. The reaction is generally conducted at from 0° C. to 100° C., although preferably at room temperature, and is generally complete from within 1 to 24 hours. The resulting reagent, X, may be isolated by conventional procedures such as extraction, filtration, chromatography, distillation, and the like. Alternatively and preferably, the reagent is not isolated from the reaction solution but an essentially equimolar amount of the amine, IX, is added to the system. Reaction pressure for this reaction is not critical and for convenience, the reaction is generally conducted at atmospheric pressure. After addition of IX, the reaction is generally conducted at room temperature and is generally complete from within 1 to 24 hours. The product, Ia, is then isolated by conventional procedures such as extraction, filtration, chromatography, distillation, or alternatively, used in Reaction (5) without purification and/or isolation.

Alternatively, product Ia may be prepared by Reaction (4a) using the acid chloride XI corresponding to $R^2CO_2H$. Acid chloride XI may be conveniently prepared by combining approximately equimolar amounts of $R^2CO_2H$ and thionyl chloride. The reaction is conducted in the liquid phase using an inert organic solvent such as methylene chloride, toluene, chloroform, and the like. It is preferred to conduct the reaction in the presence of a catalytic amount of dimethylformamide. The reaction mixture is heated to reflux and refluxed for about 0 to about 24 hours. The mixture is stirred until gas evolution ceases. After the temperature of the mixture returns to room temperature, XI may be used in Reaction (4a) without purification or isolation. Since XI is susceptible to hydrolysis, minimal handling of it is preferred.

Reaction (4a) is conducted by combining XI, with IX and IVa. The reaction is conducted in the liquid phase using an inert organic solvent such as methylene chloride, chloroform, toluene, and the like. Suitable acid scavengers, $b_2$ (IVa), include bases such as triethylamine, pyridine, an alkyl amine, sodium carbonate, and the like. The reaction is carried out at a temperature of about $-25°$ C. to about 100° C., preferably from about 0° C. to about 25° C., and may be conveniently carried out at room temperature. The reaction is generally complete within about 0 to about 24 hours. Product Ia is then isolated by conventional procedures such as extraction, filtration, chromatography, distillation, or alternatively, used in Reaction (5) without purification and/or isolation.

Reaction (5) is conducted by adding an essentially equimolar amount of phosphorus pentasulfide, XII, to Ia. The reaction is conducted in the liquid phase using an inert anhydrous organic solvent such as toluene, tetrahydrofuran, and the like. Preferably, the system is exposed to microwave radiation in order to facilitate the dispersion of phosphorus pentasulfide into solution. Reaction pressure is not critical and for convenience, the reaction is generally conducted at atmospheric pressure. The reaction is generally conducted at from 15° C. to 100° C., althouth preferably it is conducted at the ambient temperature and is generally complete from within 1 to 48 hours. The product Ib is then isolated by conventional procedures such as extraction, filtration, chromatography, distillation, and the like.

UTILITY

The compounds of the invention are effective in controlling fungal infections. Some of the compounds of this invention are particularly effective in controlling powdery mildew fungal infections caused by the organism *Erysiphe polygoni*. Some of the compounds of this invention are also useful for controlling leaf blights caused by organisms such as *Phytophthora infestans conidia*, *Alternaria solani conidia*, and *Septoria apii*. Some of the compounds of this invention are also useful for controlling fungal infections caused by *Uromyces phaseoli tipica*, *Plasmopara viticola*, and *Piricularia oryzae*. However, some fungicidal compounds of this invention may be more fungicidally active than others against particular fungi.

When used as fungicides, the compounds of the invention are applied in fungicidally effective amounts to fungi and/or their habitats, such as vegetative hosts and non-vegetative hosts, e.g., animal products. The amount used will, of course, depend on several factors such as the host, the type of fungus, and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersants. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols and polyvinyl alcohols; polyethylene oxides; sulfonated animal and vegetable oils; sulfonated petroleum oils; fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5% to 95% of the toxicant by weight of the fungicidal composition.

The fungicidal compositions may be formulated and applied with other active ingredients, including other fungicides, insecticides, nematocides, bactericides, plant-growth regulators, fertilizers, etc.

A further understanding of the invention can be had in the following non-limiting Examples. Wherein, unless expressly stated to the contrary, all temperature ranges refer to the Centigrade system and the term "ambient" or "room temperature" refers to about 20° C. to 25° C. The term "percent" refers to gram moles. The term "equivalent" refers to a quantity of reagent equal in moles, to the moles of the preceding or succeeding reagent recited in that example in terms of finite moles or finite weight or volume. Also, unless expressly stated to the contrary, geometric isomer and racemic mixtures are used as starting materials and correspondingly, isomer mixtures are obtained as products.

Compounds which were prepared in accordance with Examples 1 through 4 below are found in Table I.

EXAMPLES

Example 1

Preparation of α-bromo-(2',4',6'-trichlorophenyl)acetamide 2,4,6-trichloroaniline, 49.1 gm, was added to 250 ml of methylene chloride. The solution was cooled to 0° C. to 5° C. After cooling, 34.8 gm of triethylamine was added to the system. Then 21.8 ml of bromoacetyl bromide was added and the system allowed to warm to room temperature. The system was stirred at room temperature for 18 hours. The reaction was then stopped and the methylene chloride solution was washed with saturated sodium bicarbonate solution. The methylene chloride layer was separated and partially stripped when a solid precipitated. The solid was filtered and air dried to yield 41.4 gm of the α-bromo-(2',4',6'-trichlorophenyl)acetamide as a gray solid.

Example 2

Preparation of N-(2,4,6-trichlorophenyl)-N'-(n-propyl)glycinamide

α-bromo-(2',4',6'-trichlorophenyl)acetamide, 41.4 gm, was added to 100 ml of n-propylamine. The system was heated overnight at reflux. The excess n-propylamine was then stripped. The residue was dissolved in methylene chloride and washed with water. The solid precipitate (unreacted acetanilide) was filtered. The methylene chloride solution was removed by stripping to give 15.1 gm of N-(2,4,6-trichlorophenyl)-N'-(n-propyl)glycinamide.

Example 3

Preparation of N-(2,4,6-trichlorophenyl)-N'-(n-propyl)ethylenediamine

N-(2,4,6-trichlorophenyl)-N'-(n-propyl)glycinamide, 28.7 gm, was added to 150 ml of toluene. 18.4 ml of borane methyl sulfide (2 equivalents) was then slowly added to the system. The system was heated at approximately 60° C. for 48 hours at which time reaction completion was checked by IR spectroscopy. 100 ml of methanol was then slowly added to the system. After addition of the methanol, the system was acidified by bubbling in HCl gas. Afterwards, the system was refluxed for 1 hour. The solvent was then removed by stripping. The resulting oil as dissolved in methanol which was then stripped. The oil was next dissolved in methylene chloride. The organic solution was washed with a sodium hydroxide solution and then with water. The methylene chloride was removed by stripping to give 17.5 gm of the N-(2,4,6-trichlorophenyl)-N'-(n-propyl)ethylenediamine as an amber oil.

Example 4

Preparation of N-(2,4,6-trichlorophenyl)-N'-(n-propyl), N'-(3-pyridylcarbonyl)ethylenediamine (a) 3-pyridine carboxylic acid, 5.0 gm, was added to 15 ml of methylene chloride. 6.4 gm of carbonyldiimidazole was added to the system. The system was stirred at room temperature for 16 hours to give the 3-pyridyl carboxylic acid imidazolide.

(b) N-(2,4,6-trichlorophenyl)-N'-(n-propyl)ethylenediamine, 5.6 gm, was then added to the system. The system was stirred at room temperature for 24 hours. The reaction was then stopped and the methylene chloride solution was washed with a sodium bicarbonate solution and then with water. The methylene chloride solution was dried over magnesium sulfate and the methylene chloride removed by stripping to give 2.55 gm of N-(2,4,6-trichlorophenyl)-N'-(n-propyl), N'-(3-pyridylcarbonyl)ethylenediamine as a reddish brown oil and listed as Compound No. 1, Table I.

By following the procedures of Examples 1 to 4 and using the appropriate starting materials and reagents, the following compounds are prepared:

N-(2,4,6-trichlorophenyl)-N'-(n-propyl), N'-(2-pyrazinylcarbonyl)ethylenediamine;

N-(2,4,6-trichlorophenyl)-N'-(n-propyl), N'-(3-pyridylcarbonyl)ethylenediamine;

N-(2,4,6-tribromophenyl)-N'-(n-propyl), N'-(5-pyrimidylcarbonyl)ethylenediamine;

N-(2,4,6-trichlorophenyl)-N'-(n-propyl), N'-(1-methyl-5-imidazolylcarbonyl)ethylenediamine;

N-(4-t-butylphenyl)-N'-(n-propyl), N'-(5-pyrimidylcarbonyl)ethylenediamine;

N-(2,4,6-trichlorophenyl)-N'-allyl, N'-(3-pyridylcarbonyl)ethylenediamine;

N-(4,6-dichlorophenyl)-N'-(2-chloroallyl), N'-(3-pyridylcarbonyl)ethylenediamine;

N-(4-t-butylphenyl)-N'-(2-bromoallyl), N'-(5-pyrimidylcarbonyl)ethylenediamine;

N-(2,4,6-trichlorophenyl)-N'-(methoxyethyl), N'-(3-pyridylcarbonyl)ethylenediamine;

N-(2,4,6-tribromophenyl)-N'-(ethoxyethyl), N'-(1-methyl-5-imidazolylcarbonyl)ethylenediamine;

N-(2,4,6-triiodophenyl)-N'-(ethoxyethyl), N'-(1-methyl-5-imidazolylcarbonyl)ethylenediamine;

N-(2,4,6-trichlorophenyl)-N'-(methylthioethyl), N'-(3-pyridylcarbonyl)ethylenediamine;

N-(4-t-butylphenylether)-N'-(propargyl), N'-(3-pyridylcarbonyl)ethylenediamine;

N-phenyl-N'-chloromethyl, N'-(5-pyrimidylcarbonyl)ethylenediamine;

N-(4-methylphenyl)-N'-bromomethyl, N'-(2-pyrazinylcarbonyl)ethylenediamine;

N-(4-ethylphenyl)-N'-(2,2,2-trichloroethyl), N'-(3-pyridylcarbonyl)ethylenediamine;

N-(2,6-dimethylphenyl)-N'-(ethylthioethyl), N'-(3-pyridylcarbonyl)ethylenediamine;

N-phenyl-N'-(2-hydroxyethyl), N'-(1-methyl-5-imidazolylcarbonyl)ethylenediamine;

N-(2,4,6-trichlorophenyl)-N'-(n-propyl), N'-(3-pyridylcarbonyl)propylenediamine;

N-(2,4,6-trichlorophenyl)-N'-(n-propyl), N'-(3-pyridylcarbonyl)2-methylpropylenediamine;

N-(2,4,6-trichlorophenyl)-N'-(n-propyl), N'-(3-pyridylcarbonyl)butylenediamine;

N-(2,4,6-trichlorophenyl)-N'-(n-propyl), N'-(3-pyridylcarbonyl)2,2-dimethylpropylenediamine;

N-(2,4,6-trichlorophenyl)-N'-(n-propyl), N'-(3-pyridylcarbonyl)2-ethylpropylenediamine;

N-(2,4,6-trichlorophenyl)-N'-allyl, N'-(2-pyrazinylcarbonyl)2,3-dimethylbutylenediamine;

N-(2,4,6-trichlorophenyl)-N-(n-propyl)-N'-(3-pyridylthiocarbonyl)ethylenediamine;

N-(4-t-butylphenyl)-N'-(2-pyrazinylthiocarbonyl), N'-(n-propyl)ethylenediamine;

N-(2,4,6-trimethylphenyl)-N'-(2-chloroethyl)-N'-(5-pyrimidylthiocarbonyl)ethylenediamine; and N-(4-trifluoromethylphenyl)-N'-(n-propyl)-N'-(3-pyridylcarbonyl)ethylenediamine.

EXAMPLE A

Bean Powdery Mildew

The compounds of the invention were tested for the control of the Bean Powdery Mildew organism *Erysiphe polygoni*. Seedling bean plants were sprayed with a 250-ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. The percent disease control provided by a given test compound was based on the percent disease reduction relative to the untreated check plants. The results are tabulated in Table II.

EXAMPLE B

Tomato Late Blight

Compounds of the invention were tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a nonionic emulsifier. The sprayed plants were then inoculated 1 day later with the organism, placed in an environmental chamber and incubated at 66° F. to 68° F. and 100% relative humidity for at least 16 hours. Following the incubation, the plants were maintained in a greenhouse for approximately 7 days. The percent disease control provided by a given test compound was based on the percent disease reduction relative to untreated check plants. The results are tabulated in Table II.

EXAMPLE C

Celery Late Blight

The Celery Late Blight tests were conducted using celery (Utah) plants 11 weeks old. The Celery Late Blight organism was *Septoria apii*. The celery plants were sprayed with 250-ppm solutions of the candidate toxicant mixed with acetone, water and a nonionic emulsifier. The plants were then inoculated with the organism and placed in an environmental chamber and incubated at 66° F. to 68° F. in 100% relative humidity for an extended period of time (approximately 48 hours). Following the incubation, the plants were allowed to dry and then were maintained in a greenhouse for approximately 14 days. The percent disease control provided by a given candidate toxicant is based on the percent disease reduction relative to untreated check plants. The results are reported in Table II.

EXAMPLE D

Tomato Early Blight

Compounds of the invention were tested for the control of the Tomato Early Blight organism *Alternaria solani conidia*. Tomato (variety Bonny Best) seedlings of 6- to 7-weeks old were used. The tomato plants were sprayed with a 250-ppm solution of the test compound in an acetone-and-water solution containing a small amount of a nonionic emulsifier. The sprayed plants were inoculated 1 day later with the organism, placed in the environmental chamber and incubated at 66° F. to 68° F. and 100% relative humidity for 24 hours. Following the incubation, the plants were maintained in a greenhouse for about 12 days. Percent disease control was based on the percent disease development on untreated check plants. The compounds tested and the results are tabulated in Table II.

EXAMPLE E

Grape Downy Mildew

The compounds of the invention were tested for the control of the Grapy Downy Mildew organism *PLasmopara viticola*. Detached leaves, between 70 mm and 85 mm in diameter, 7-week-old *Vitis vinifera* cultivar Emperor grape seedlings were used as hosts. The leaves were sprayed with a 250-ppm solution of the test compound in acetone. The sprayed leaves were dried, inoculated with a spore suspension of the organism, placed in a humid environmental chamber and incubated at 66° F. to 68° F. and about 100% relative humidity. After incubation for 2 days, the plants were then held in a greenhouse 7 to 9 days; then the amount of disease control was determined. The percent disease control provided by a given test compound was based on the percent disease reduction relative to untreated check plants. The results are tabulated in Table II.

EXAMPLE F

Leaf Rust

The Leaf Rust test was made using pinto beans. The pathogen was *Uromyces phaseoli tipica*. The pinto bean plants were sprayed with a 250-ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68° F. to 70° F. The plants were then removed from the chamber, allowed to dry, and then maintained in a greenhouse at a 60% to 80% relative humidity. The rate of infection on the leaves was made after about 14 days. The percent disease control provided by a given test compound was based on the percent disease reduction relative to untreated check plants. The results are reported in Table II.

EXAMPLE G

Rice Blast

Compounds of this invention were tested for control of the Rice Blast organism *Piricularia oryzae*, using 10- to 14-day-old rice plant seedlings (Calrose M-9 variety). Seedling plants were sprayed with a 625-ppm solution of the test compound in acetone, water and a nonionic emulsifier (ORTHO X-77 spreader). The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 72° F. and maintained with bottom watering for about 12 to 16 days. The percent disease control provided by a given test compound is based on a comparison of the percentage disease relative to the percent disease development on the untreated check plants:

$$\% \text{ Control} = 100 \times \left( \frac{\% \text{ disease in treated plants}}{\% \text{ disease in check}} \right)$$

The results are tabulated in Table II.

TABLE I

Compounds Of The Formula:

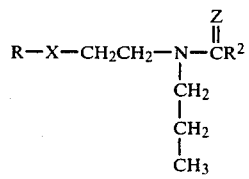

| Compound No. | Z | X | R | R² | ANALYSIS | | | | | | Form | m.p. |
|---|---|---|---|---|---|---|---|---|---|---|---|---|
| | | | | | Carbon | | Hydrogen | | Nitrogen | | | |
| | | | | | Calc. | Found | Calc. | Found | Calc. | Found | | |
| 1 | O | NH | 2,4,6-trichlorophenyl | pyridyl | 52.79 | 51.88 | 4.69 | 4.83 | 10.86 | 10.52 | oil | 75°— |
| 2 | O | NH | 2,4,6-trichlorophenyl | pyrazinyl | 49.56 | 49.42 | 4.42 | 4.45 | 14.45 | 14.95 | white solid | 77° C. |

TABLE II

| Compound No. | Fungicidal Activity Control | | | | | | |
|---|---|---|---|---|---|---|---|
| | GDM | TLB | CLB | TEB | BR | BPM | RB |
| 1 | 0 | 0 | 29 | 27 | 0 | 56 | 0 |
| 2 | 31 | 0 | 29 | 0 | 0 | 0 | 38 |

GDM - Grape Downy Mildew (*Plasmopara viticola*)
TLB - Tomato Late Blight (*Phytophthora infestans*)
CLB - Celery Late Blight (*Septoria apii*)
TEB - Tomato Early Blight (*Alternaria solani conidia*)
BR - Bean Rust (*Uromyces phaseoli tipica*)
BPM - Bean Powdery Mildew (*Erysiphe polygoni*)
RB - Rice Blast (*Piricularia oryzae*)

What is claimed is:

1. A compound of the formula:

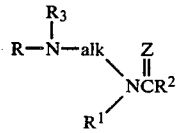

wherein R is phenyl, or phenyl substituted with 1 to 3 substituents independently selected from fluoro, chloro, bromo, iodo, nitro, lower alkyl, lower alkoxy, lower alkyl or lower alkoxy substituted with 1 to 3 of the same or different halogens; $R^1$ is lower alkyl, or —$CH_2Y$ wherein Y is lower alkenyl, lower alkenyl substituted with 1 to 3 of the same or different halogens, lower alkynyl, lower alkynyl substituted with 1 to 3 of the same or different halogens, lower alkoxyalkyl, lower alkoxy, lower alkylthioalkyl, lower thioalkyl, lower hydroxyalkyl, lower haloalkyl, or halogen; $R^2$ is pyridyl or pyridyl substituted with 1 to 2 independent lower alkyl groups, with the proviso that a nitrogen of the pyridyl ring is not bonded to the $$-\overset{\overset{Z}{\|}}{C}-$$

group; $R^3$ is hydrogen or lower alkyl; Z is sulfur, or oxygen; and alk is both branched- and straight-chain alkylene groups of 1 to 10 carbons with the proviso that the chain length is no longer than 5 carbons.

2. A compound of the formula defined in claim 1 wherein $R^1$ is lower alkyl or $CH_2Y$ wherein Y is lower alkenyl, lower alkynyl, lower alkoxyalkyl, lower alkoxy, lower hydroxyalkyl, lower haloalkyl or halogen.

3. A compound of the formula described in claim 2 wherein $R^1$ is lower alkyl.

4. A compound of the formula defined in claim 3 wherein $R^1$ is propyl.

5. A compound of the formula defined in claim 1 wherein R is phenyl substituted with 1 to 3 substituents selected from fluoro, chloro, bromo, iodo, nitro, lower alkyl, lower alkoxy or lower alkyl substituted with 1 to 3 halogens.

6. A compound of the formula defined in claim 5 wherein R is phenyl substituted with 1 to 3 halogens.

7. A compound of the formula defined in claim 6 wherein R is 2,4,6-trihalophenyl.

8. A compound of the formula defined in claim 7 wherein R is 2,4,6-trichlorophenyl.

9. A compound of the formula defined in claim 1 wherein $R^2$ is 3-pyridyl.

10. A compound of the formula defined in claim 9 wherein R is 2,4,6-trichlorophenyl, $R_1$ is propyl, $R_3$ is hydrogen, Z is oxygen and alk is ethylene.

11. A fungicidal composition comprising a biologically inert carrier and a fungicidally effective amount of a compound of the formula defined in claim 1.

12. A fungicidal composition comprising a biologically inert carrier and a fungicidally effective amount of a compound of the formula defined in claim 3.

13. A fungicidal composition comprising a biologically inert carrier and a fungicidally effective amount of a compound of the formula defined in claim 10.

14. A method for controlling fungi comprising contacting said fungi or their growth environment with a fungicidally effective amount of a compound of the formula defined in claim 1.

15. A method for controlling fungi comprising contacting said fungi or their growth environment with a fungicidally effective amount of a compound of the formula defined in claim 3.

16. A method for controlling fungi comprising contacting said fungi or their growth environment with a fungicidally effective amount of a compound of the formula defined in claim 10.

* * * * *